(12) United States Patent
Palin et al.

(10) Patent No.: US 11,607,127 B2
(45) Date of Patent: Mar. 21, 2023

(54) TRANSFER OF SENSOR DATA

(71) Applicant: NOKIA TECHNOLOGIES OY, Espoo (FI)

(72) Inventors: Arto Palin, Akaa (FI); Jukka Reunamäki, Tampere (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 918 days.

(21) Appl. No.: 16/465,223

(22) PCT Filed: Nov. 30, 2016

(86) PCT No.: PCT/FI2016/050847
§ 371 (c)(1),
(2) Date: May 30, 2019

(87) PCT Pub. No.: WO2018/100229
PCT Pub. Date: Jun. 7, 2018

(65) Prior Publication Data
US 2019/0349769 A1 Nov. 14, 2019

(51) Int. Cl.
*A61B 5/00* (2006.01)
*H04W 76/10* (2018.01)
(Continued)

(52) U.S. Cl.
CPC .......... *A61B 5/0022* (2013.01); *A61B 5/0002* (2013.01); *A61B 5/024* (2013.01);
(Continued)

(58) Field of Classification Search
CPC ..... A61B 5/0022; A61B 5/0002; A61B 5/024; A61B 5/1118; A61B 5/117; A61B 5/01;
(Continued)

(56) References Cited

U.S. PATENT DOCUMENTS 9,063,164 B1 * 6/2015 Yuen .................... G01C 22/006
2010/0318578 A1 12/2010 Treu et al.
(Continued)

FOREIGN PATENT DOCUMENTS

| CN | 104684466 A | 6/2015 |
| EP | 2 958 354 A1 | 12/2015 |
| WO | WO 2017/182694 A1 | 10/2017 |

OTHER PUBLICATIONS

Extended European Search Report dated May 8, 2020 corresponding to European Patent Application No. 16922916.8.
(Continued)

*Primary Examiner* — Tanmay K Shah
(74) *Attorney, Agent, or Firm* — Squire Patton Boggs (US) LLP

(57) ABSTRACT

According to an example embodiment, there is provided a method in a device (110) that comprises a sensor portion (119) for deriving, on basis of one or more sensor signals that are descriptive of respective physical characteristic pertaining to a user, at least one measurement signal that is descriptive of a characteristic pertaining to the user, the method comprising obtaining first measurement data that comprises one or more values indicated by the at least one measurement signal and transferring the first measurement data to a server device (150) over a first wireless link (104), receiving, from the server device (150), device information that comprises at least a device identifier and access information for another device that is capable of providing second measurement data that is descriptive of one or more characteristics pertaining to the same user, in response to receiving said device information, detecting presence of said another device (130) and establishing a second wireless link (106) with said another device (130) using said device information, and receiving the second measurement data from said another device (130) via the second wireless link
(Continued)

(106) and transferring the second measurement data to the server device (150) via the first wireless link (104).

20 Claims, 6 Drawing Sheets

(51) Int. Cl.
*A61B 5/024* (2006.01)
*A61B 5/11* (2006.01)
*A61B 5/117* (2016.01)
*G01G 19/50* (2006.01)
*H04W 8/00* (2009.01)
*H04W 12/069* (2021.01)

(52) U.S. Cl.
CPC ............. *A61B 5/117* (2013.01); *A61B 5/1118* (2013.01); *G01G 19/50* (2013.01); *H04W 8/005* (2013.01); *H04W 12/069* (2021.01); *H04W 76/10* (2018.02)

(58) Field of Classification Search
CPC ..... A61B 5/021; A61B 5/02438; A61B 5/681; A61B 5/6823; G01G 19/50; H04W 8/005; H04W 12/069; H04W 76/10; H04W 12/33; H04W 4/38; H04W 8/18; H04W 84/18; G16H 40/63; G16H 40/67; G16Z 99/00; H04L 63/0861
USPC .......................................................... 713/182
See application file for complete search history.

(56) References Cited

U.S. PATENT DOCUMENTS

| 2012/0079019 | A1 | 3/2012 | Miettinen et al. |
| 2012/0182939 | A1 | 7/2012 | Rajan et al. |
| 2014/0039328 | A1 | 2/2014 | Kampman et al. |
| 2014/0118159 | A1* | 5/2014 | Fish ..................... A61B 5/0022 340/870.01 |
| 2014/0121540 | A1 | 5/2014 | Raskin |
| 2015/0081763 | A1 | 3/2015 | Sipola et al. |
| 2015/0180842 | A1 | 6/2015 | Panther |
| 2016/0189451 | A1 | 6/2016 | Yoo et al. |
| 2017/0068785 | A1* | 3/2017 | Experton ............ G06F 21/6245 |

OTHER PUBLICATIONS

Notification of Second Office Action dated Dec. 2, 2021 corresponding to Chinese Patent Application No. 201680092003X, with English summary thereof.
Rejection Decision dated Apr. 8, 2022 corresponding to Chinese Patent Application No. 201680092003.X, with English Summary thereof.
International Search Report and Written Opinion dated Mar. 15, 2017 corresponding to International Patent Application No. PCT/FI2016/050847.
Notification of the First Office Action dated Jul. 5, 2021 corresponding to Chinese Patent Application No. 201680092003.X, with English Summary thereof.
Communication pursuant to Article 94(3) EPC dated Dec. 6, 2022 corresponding to European Patent Application No. 16922916.8.

* cited by examiner

TRANSFER OF SENSOR DATA

TECHNICAL FIELD

The example and non-limiting embodiments of the present invention relate to transfer of sensor data pertaining to a user extracted by one or more monitoring devices in an efficient and user-friendly manner.

BACKGROUND

Different kind of activity monitors and monitoring devices of other type that collect sensor data measured from a user have become more and more popular. A single user may have multiple devices that each collect respective sensor data pertaining to the same user, such as activity data and health related data. Collection of such data may be continuous or it may take place from time to time, either autonomously or in response to a user action. In one viewpoint, such monitoring devices may be considered as Internet of Things (IoT) sensor devices that serve to measure certain predefined parameters, such as the number of steps taken by the user or the weight of the user and provide measured values to a remote server for storage and/or analysis therein.

In a typical scenario, a monitoring device is locally connected to a mobile device of the user and relies on a specific application installed on the mobile device, which application then enables uploading the measured values to the remote server via user operating the application.

SUMMARY

According to an example embodiment, there is provided a method in a device that comprises a sensor portion for deriving, on basis of one or more sensor signals that are descriptive of respective physical characteristic pertaining to a user, at least one measurement signal that is descriptive of a characteristic pertaining to the user, the method comprising obtaining first measurement data that comprises one or more values indicated by the at least one measurement signal and transferring the first measurement data to a server device over a first wireless link, receiving, from the server device, device information that comprises at least a device identifier and access information for another device that is capable of providing second measurement data that is descriptive of one or more characteristics pertaining to the same user, in response to receiving said device information, detecting presence of said another device and establishing a second wireless link with said another device using said device information, and receiving the second measurement data from said another device via the second wireless link and transferring the second measurement data to the server device via the first wireless link.

According to another example embodiment, a device is provided, the device comprising a sensor portion for deriving, on basis of one or more sensor signals that are descriptive of respective physical characteristic pertaining to a user, at least one measurement signal that is descriptive of a characteristic pertaining to the user, a communication apparatus for wireless communication over a wireless link, and a control portion arranged to cause the device to perform at least the following: obtain first measurement data that comprises one or more values indicated by the at least one measurement signal and transfer the first measurement data to a server device over a first wireless link, receive, from the server device, device information that comprises at least a device identifier and access information for another device that is capable of providing second measurement data that is descriptive of one or more characteristics pertaining to the same user, in response to receiving said device information, detect presence of said another device and establish a second wireless link with said another device using said device information, and receive the second measurement data from said another device via the second wireless link and transfer the second measurement data to the server device via the first wireless link.

According to another example embodiment, a device is provided, the device comprising a sensor means for deriving, on basis of one or more sensor signals that are descriptive of respective physical characteristic pertaining to a user, at least one measurement signal that is descriptive of a characteristic pertaining to the user, a communication means for wireless communication over a wireless link, and a control means for causing the device to perform at least the following: obtain first measurement data that comprises one or more values indicated by the at least one measurement signal and transfer the first measurement data to a server device over a first wireless link, receive, from the server device, device information that comprises at least a device identifier and access information for another device that is capable of providing second measurement data that is descriptive of one or more characteristics pertaining to the same user, in response to receiving said device information, detect presence of said another device and establish a second wireless link with said another device using said device information, and receive the second measurement data from said another device via the second wireless link and transfer the second measurement data to the server device via the first wireless link.

According to another example embodiment, a computer program is provided, the computer program comprising computer readable program code configured to cause performing at least the method according to the example embodiment described in the foregoing when said program code is executed on a computing apparatus:

The computer program according to an example embodiment may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

Some features of the invention are set forth in the appended claims. Aspects of the invention, however, both as to its construction and its method of operation, together with additional objects and advantages thereof, will be best understood from the following description of some example embodiments when read in connection with the accompanying drawings.

BRIEF DESCRIPTION OF FIGURES

The embodiments of the invention are illustrated by way of example, and not by way of limitation, in the figures of the accompanying drawings, where FIG. 1 schematically illustrates some components of a wireless communication arrangement according to an example embodiment.

DESCRIPTION OF SOME EMBODIMENTS

Figure 1:
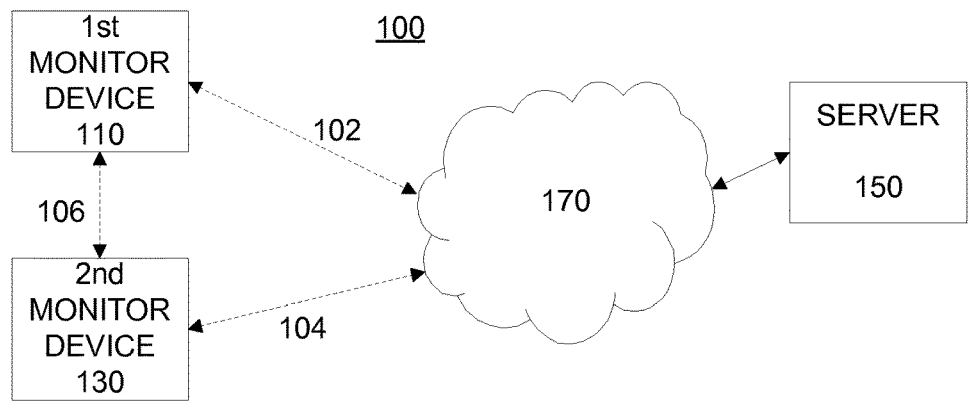

FIG. 1 schematically illustrates a block diagram of some components and/or entities of a wireless communication arrangement 100 to depict an exemplifying framework for one or more embodiments of the present invention. The wireless communication arrangement 100 comprises a first monitoring device 110 for capturing sensor data pertaining to a user, a second monitoring device 130 for capturing sensor data pertaining to the (same) user and a server device 150 for storing and/or processing the sensor data captured by the first and second monitoring devices 110, 130. The first monitoring device 110 is connectable to a network 170 via a first wireless link 102, thereby enabling a connection between the first monitoring device 110 and the server device 150 via the network 170. The second monitoring device 130 is connectable to other devices, e.g. to the first monitoring device 110, via a second wireless link 106. The second monitoring device 130 may be further connectable to the network 170 via a third wireless link 104, thereby enabling a connection between the second monitoring device 130 and the server device 150 via the network 170.

The first monitoring device 110 may employ (a first set of) one or more sensors for capturing respective sensor signals that are descriptive of respective physical characteristics pertaining to a user and to generate, on basis of the captured sensor signals, one or more measurement signals. The measurement signal(s) generated in the first monitoring device 110 or information extracted from the generated measurement signals are stored in the first monitoring device 110 and/or transferred from the first monitoring device 110 to the server device 150.

The second monitoring device 130 may employ (a second set of) one or more sensors to capture respective sensor signals that are descriptive of respective physical characteristics pertaining to the same user as the sensor signals captured in the first monitoring device 110 and to generate, on basis of the captured sensor signals, one or more measurement signals. The measurement signals generated in the second monitoring device 130 or information extracted from the generated measurement signals are stored in the second monitoring device 130 and/or transferred from the second monitoring device 130 to the server device 150. The transfer may be carried out via the wireless link 104 in response to a user action or the transfer may be carried autonomously via the wireless link 106 and hence via the first monitoring device 110 according to procedures described via a number of examples in the following.

The examples described in the foregoing and in the following refer to a measurement signal that is descriptive of a certain characteristic pertaining to a user in singular. This, however, is a choice made in favor of editorial clarity of the description, and in other examples the measurement signal may consist of two or more distinct signals (e.g. sub-signals) that are jointly descriptive of the certain characteristic pertaining to the user.

Figure 2:
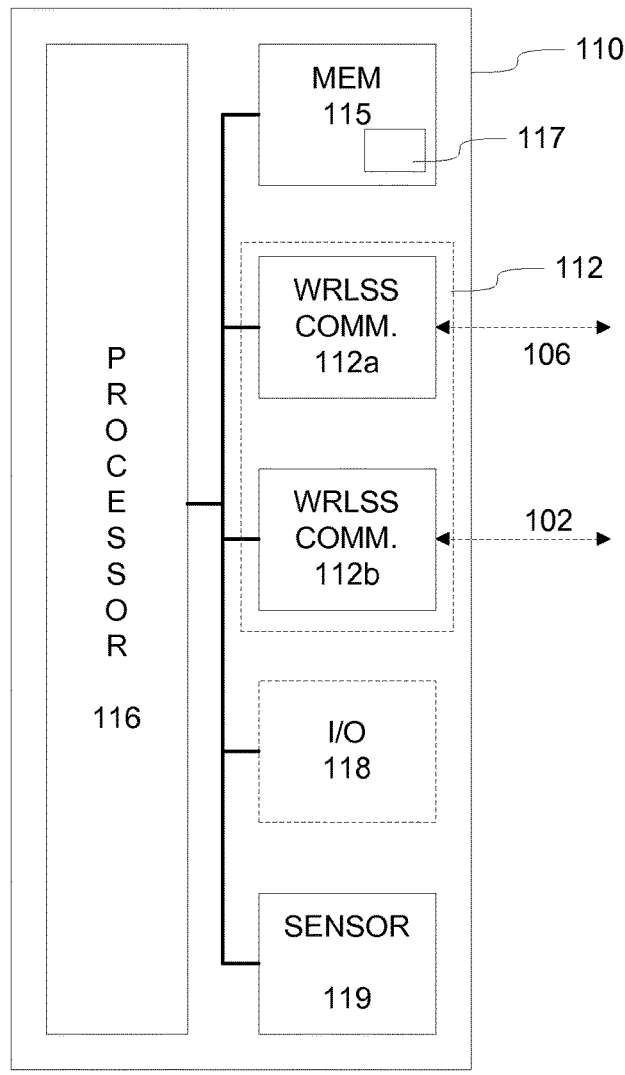
FIG. 2 schematically illustrates some components of a monitoring device according to an example embodiment.

FIG. 2 depicts a block diagram of some components of an exemplifying first monitoring device 110. The first monitoring device 110 may comprise further components or portions in addition to those depicted in FIG. 2. In this regard, the first monitoring device 110 further comprises e.g. a power supply for providing electrical power to components of the first monitoring device 110. The power supply may comprise, e.g. a rechargeable or non-rechargeable battery, which battery may be replaceable or it may be installed in the first monitoring device 110 in a fixed manner. Alternatively, the first monitoring device 110 may comprise an interface for receiving electrical power e.g. from the mains electricity.

The first monitoring device 110 is typically provided as a portable device that can be conveniently carried to the site of its usage but that is not an actual mobile device that is frequently or constantly carried by the user due to its shape, size, weight and/or function. Such device is typically a special-purpose device having generation of the measurement signal(s) and their transfer to the server device 150 as its sole function or as one of its main functions. In another example, the first monitoring device 110 is installed to its site in a fixed or semi-fixed manner and the usage of the first monitoring device is assumed to primarily take place at this site. In a way, such device is a stationary device that is not expected to be transferred from from its site of usage and/or is only exceptionally relocated to another site. In a further example, the first monitoring device 110 may be provided as a special-purpose mobile device that has generation of the measurement signal(s) and their transfer to the server device 150 as one of its main functions.

The first monitoring device 110 comprises a communication portion 112. The communication portion 112 comprises at least a first communication apparatus 112a for wireless communication with other apparatuses and it may further comprise a second communication apparatus 112b for wireless communication with other apparatuses. The communication portion 112 may comprise one or more further communication apparatuses for wireless and/or wired communication with other apparatuses. The first communication apparatus 112a may enable, for example, wireless communication with other devices by using a wireless communication technique or protocol that enables a point-to-point or a point-to-multipoint wireless connection with another device. The first communication apparatus 112a may be employed to establish the wireless link 106 that enables wireless communication with the second monitoring device 130. The second communication apparatus 112b, if included in the first monitoring device 110, may apply communication technique/protocol different from that of the first communication apparatus 112a and it may enable establishing the wireless link 102 to the network 170, which in turn enables communication with the server device 150.

The first monitoring device 110 further comprises a processor 116 and a memory 115 for storing data and computer program code 117. The first monitoring device 110 may further comprise user I/O (input/output) components 118 that may be arranged, possibly together with the processor 116 and a portion of the computer program code 117, to provide a user interface (UI) for receiving input from a user of the first monitoring device 110 and/or providing output to the user of the first monitoring device 110. The user I/O components 118 may comprise hardware components such as a display, a touchscreen, a touchpad, a keyboard, and/or an arrangement of one or more keys or buttons, etc. The processor 116 may be arranged to control operation of the first monitoring device 110 e.g. in accordance with a portion of the computer program code 117 stored in the memory 115 and possibly further in accordance with the user input received via the user I/O components 118 and/or in accordance with information received via the communication portion 112. The memory 115 and a portion of the computer program code 117 stored therein may be further arranged to, with the processor 116, to provide a control portion or a control function for controlling operation of a communication apparatus of the communication portion 112, possibly together with a control portion or a control function that may be provided within the respective communication apparatus of the communication portion 112 (which will be described later in this text). These control functions may be, separately or jointly, referred to as control means (of the first monitoring device 110).

The first monitoring device 110 further comprises a sensor portion 119 for deriving one or more first measurement signals, where each first measurement signal is descriptive of a respective characteristic pertaining to the user. The sensor portion 119 may include one or more first sensors for capturing respective first sensor signals, where each first sensor signal is descriptive of a physical characteristic associated with the user. The one or more first sensor signals are used as basis for generating the one or more first measurement signals. In a straightforward example, a first sensor signal, i.e. a sensor signal captured by a respective one of the one or more first sensors, is provided as such as the respective first measurement signal. In another example the sensor portion 119 comprises an analysis portion (not shown in FIG. 2) that is arranged to derive each of the first measurement signals on basis of one or more first sensor signals. In an example, a first measurement signal is indicative of an instantaneous value of a certain characteristic pertaining to the user. In another example, a first measurement signal is indicative of an average value of a certain characteristic pertaining to the user, computed over a predefined time period. In a further example, a first measurement signal is indicative of the value of a certain characteristic pertaining to the user as a function of time.

The control means may operate the sensor portion 119 and the analysis portion (if present) to obtain the one or more first measurement signals as desired and store at least part of the information carried in the one or more first measurement signals as first measurement data in the memory 115. In addition to or instead of storing the information, the control means may operate the communication portion 112 (e.g. the second communication apparatus 112b) to transfer at least part of the first measurement data to the server device 150 for subsequent analysis and/or presentation to the user. Herein, the analysis portion serves as a logical entity that may be provided, instead of being provided as part of the sensor portion 119, for example, as part of the control means or as an entity separate from the sensor portion 119 and the control means.

Figure 3:
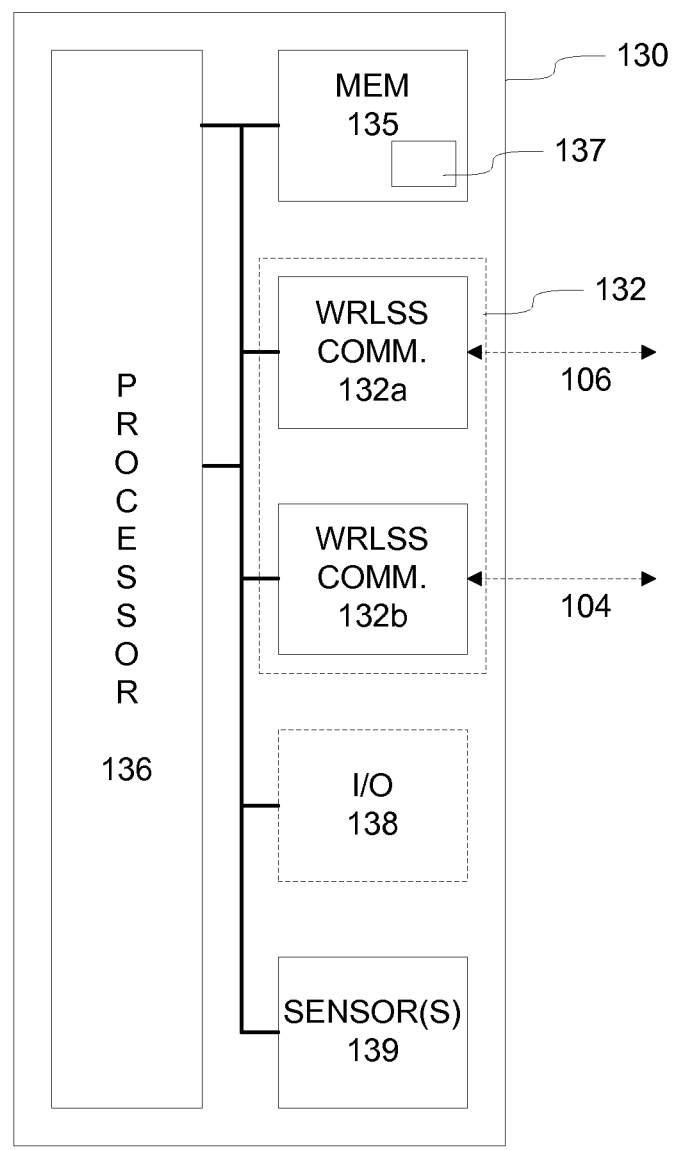
FIG. 3 schematically illustrates some components of a monitoring device according to an example embodiment.

FIG. 3 depicts a block diagram of some components of an exemplifying second monitoring device 130. The second monitoring device 130 may comprise further components or portions in addition to those depicted in FIG. 3. As an example in this regard, the second monitoring device 130 further comprises e.g. a power supply for providing electrical power to components of the secondary monitoring device 130. The power supply may comprise, e.g. a rechargeable or non-rechargeable battery, which battery may be replaceable or it may be installed in the second monitoring device 130 in a fixed manner.

The second monitoring device 130 is typically provided as a mobile device that is frequently carried by its user. As an example in this regard, the second monitoring device 130 is a mobile device that a user may carry with him/her or wear as he/she chooses. As a particular example of the latter, the first monitoring device 110 may be provided as a wearable device that the user is able to wear through wearing a fitting arrangement or an installation arrangement designed for the purpose. Such wearable devices are typically special-purpose devices that have generation of the measurement signal(s) and their transfer to the server device 150 as its sole function or as one of its main functions. Non-limiting example of such a wearable device is an activity tracker that is arranged to measure one or more characteristic that are descriptive of activity of the user and that may be provided e.g. as a wrist band or as a smart watch. Further non-limiting examples include a wireless sensor arrangement integrated to clothing and a wireless sensor arrangement that is wearable by the user by using a specially designed fitting arrangement such as a chest band. Such wearable sensor arrangement may be provided e.g. as heart rate monitor, a blood pressure meter, a glucose meter, etc.

The second monitoring device 130 comprises a communication portion 132. The communication portion 132 comprises at least a first communication apparatus 132a for wireless communication with other apparatuses and it may further comprise a second communication apparatus 132b for wireless communication with other apparatuses. The communication portion 132 may comprise one or more further communication apparatuses for wireless and/or wired communication with other apparatuses. The communication apparatus 132a may enable, for example, wireless communication with other devices by using a wireless communication technique or protocol that enables a point-to-point or a point-to-multipoint wireless connection with another device, in particular with the communication apparatus 112a. The communication apparatus 132a may hence be employed to establish the wireless link 106 that enables the second monitoring device 130 to wirelessly communicate with the first monitoring device 110. The second communication apparatus 132b, if included in the second monitoring device 130, may apply communication technique/protocol different from that of the first communication apparatus 132a and it may enable establishing the wireless link 104 to the network 170, which in turn enables communication with the server device 150.

The second monitoring device 130 further comprises a processor 136 and a memory 135 for storing data and computer program code 137. The second monitoring device 130 may further comprise user I/O (input/output) components 138 that may be arranged, together with the processor 136 and a portion of the computer program code 137, to provide a user interface (UI) for receiving input from a user of the second monitoring device 130 and/or providing output to the user of the second monitoring device 130. The user I/O components 138 may comprise hardware components such as a display, a touchscreen, a touchpad, a keyboard and/or an arrangement of one or more keys or buttons, etc. The processor 136 may be arranged to control operation of the second monitoring device 130 in accordance with a portion of the computer program code 137 stored in the memory 135 and possibly further in accordance with the user input received via the user I/O components 138 and/or in accordance with information received via the communication portion 132. The memory 135 and a portion of the computer program code 137 stored therein may be further arranged, with the processor 136, to provide a control portion or a control function for controlling operation of a communication apparatus of the communication portion 132, possibly together with a control portion or a control function that may be provided within the respective communication apparatus of the communication portion 132 (which will be described later in this text). These control functions may be, separately or jointly, referred to as control means (of the second monitoring device 130).

The second monitoring device 130 further comprises a sensor portion 139 for deriving one or more second measurement signals, where each second measurement signal is descriptive of a respective characteristic pertaining to the user. The sensor portion 139 may include one or more second sensors for capturing respective second sensor signals, where each second sensor signal is descriptive of a respective physical characteristic associated with the user. The one or more second sensor signals are used as basis for generating the one or more second measurement signals. In an example, a second sensor signal, i.e. a sensor signal captured by a respective one of the one or more second sensors, is provided as such as the respective second measurement signal. In another example the sensor portion 139 comprises an analysis portion (not shown in FIG. 3) that is arranged to derive each of the second measurement signals on basis of one or more second sensor signals. In an example, a second measurement signal is indicative of an instantaneous value of a certain characteristic pertaining to the user. In another example, a second measurement signal is indicative of the value of a certain characteristic pertaining to the user as a function of time.

The control means may operate the sensor portion 139 and the analysis portion (if present) to derive the one or more second measurement signals as desired and store at least part of the information carried in the one or more second measurement signals as second measurement data in the memory 135. In addition to or instead of storing the information, the control means may operate the communication portion 132 to transfer at least part of the second measurement to the server device 150 for subsequent analysis and/or presentation to the user. The transfer may be carried out via the wireless link 104 (e.g. by the second communication apparatus 132b) in response to a user action or the transfer may be carried autonomously via the wireless link 106 (e.g. by the first communication apparatus 132a) and hence via the first monitoring device 110. In variations of this example, the operation of the analysis portion is provided as part of the control means, or the analysis portion is provided as an entity separate from the sensor portion 139 and the control means.

The server device 150 is typically a remote server device that is arranged to provide a server function that is accessible by a number of first monitoring devices 110 and/or second monitoring device 130. Although described herein, for editorial clarity of description, as a single entity, the server function described in this text by using the server device 150 as an example may be jointly provided by a number of server devices that are arranged to provide a cloud service, a cloud server arrangement or a cloud computing arrangement.

In general, a sensor of the sensor portion 119, 139 may be any type of sensor known in the art, depending on the measurement signals to be derived by the respective monitoring device 110, 130. As a few non-limiting examples, suitable types of sensor include an accelerometer, a pressure sensor, a temperature sensor, a speed sensor, etc. The capture sensor signals, in turn, may be applied to device various types of measurement signals according to the intended usage of the monitoring device 110, 130. As a few non-limiting examples, a measurement signal may be indicative of a characteristic pertaining to a biometric characteristic of a user (such as heart rate, blood pressure, body temperature, etc.) or a characteristic pertaining to physical state of a user (such as speed of movement, number of steps taken, location of the user, etc.).

In order to provide a concrete but non-limiting examples, in the following occasional references are made to an example where the first monitoring device 110 comprises a digital weighing scale that is arranged to generate respective first measurement signals to indicate weight of the user and a heart rate of the user and where the second monitoring device 130 comprises an activity tracker provided in a wrist band that is arranged to generate respective second measurement signals to indicate one or more of the following: distance traveled by the user, the number of steps taken by the user, the speed of movement of the user, the heart rate of the user.

As described in the foregoing, the communication portion 112 may comprise communication apparatuses 112a and 112b, while the communication portion 132 may comprise communication apparatuses 132a and 132b. Each of the communication apparatuses 112a, 112b, 132a and 132b described in the foregoing may also be referred to as a respective (wireless) communication means. A communication apparatus may be provided e.g. as a respective chipset and/or as a respective communication module. For clarity and brevity of description, each of the communication apparatuses 112a, 112b, 132a and 132b may be considered as a respective single logical entity that may also be capable of processing at least some of the information received via the employed wireless link 102, 104, 106 and/or at least some of the information that is to be transmitted via the employed wireless link 102, 104, 106 without external control from other components of the respective monitoring device 110, 130 (e.g. from the processor 116, 136, respectively). In an embodiment, a communication apparatus 112a, 112b, 132a, 132b comprises e.g. a respective wireless transceiver portion for wireless communication and a respective control portion (or a control function) for controlling operation of the respective wireless transceiver portion and for processing information received/transmitted via the respective wireless transceiver portion. Such a control function may be provided by hardware means, by software means or by a combination of hardware means and software means. As an example in this regard, the communication apparatus 112a, 112b, 132a, 132b may comprise a memory, a processor, whereas a portion of a computer program code stored in the memory may be arranged to, with the processor, provide the control function for controlling operation of the respective wireless communication apparatus 112a, 112b, 132a, 132b, either independently or jointly with the control function provided by the respective memory 115, 135, a portion of the respective computer program 117, 137 and the respective processor 116, 136 of the respective monitoring device 110, 130.

The first wireless communication apparatus 112a in the communication portion 112 and the first wireless communication apparatus 132a in the communication portion 132 may be arranged to employ any suitable short-range wireless communication technique or protocol known in the art to establish the wireless link 106 between the two monitoring devices 110, 130. Such a wireless link may also be referred to as a local wireless link. The local wireless link typically involves a peer-to-peer connection between the involved devices. The term short-range wireless communication as used herein refers to a wireless communication technique or protocol that enables typical operating range in the scale of tens of meters, e.g. up to 100 meters. However, especially in an indoor environment, the operating range of such short-range wireless communication technique/protocol may be significantly shorter e.g. due to walls and other stationary structures as well as furniture etc. that are likely to partially block or interfere with the radio communication between communication apparatuses 112a, 132a. On the other hand, in favorable conditions in outdoor use the operating range may extend to several hundreds of meters.

Examples of such a short-range wireless communication technique/protocol include the Bluetooth Basic Rate/Enhanced Data Rate (BT BR/EDR) protocol and the Bluetooth Low Energy (BLE) protocol, both specified e.g. in the Bluetooth Specification Version 4.1, Covered Core Package version: 4.1 (publication date 3 Dec. 2013), incorporated herein by reference in its entirety. In the following, this document is referred to as a Bluetooth Specification. However, the BT BR/EDR and BLE technologies serve as illustrative and non-limiting examples in this regard, and the description generalizes into any short-range wireless communication technique/protocol. A further example of a suitable short-range wireless communication technique/protocol includes Wireless Local Area Network (WLAN) technology specified e.g. in IEEE 802.11 specifications (where the acronym IEEE stands for the Institute of Electrical and Electronics Engineers). Yet further examples of other suitable short-range wireless communication techniques/protocols known in the art include ANT wireless sensor network technology and IEEE 802.15.4 network technology for low-rate wireless personal networks (LR-WPANs).

The second wireless communication apparatus 112b in the communication portion 112 of the first monitoring device 110, if included therein, may be arranged to employ any suitable wireless access technology known in the art to establish the wireless link 102 that enables a connection to the network 170 that further connects the first monitoring device 110 to the server device 150. As an example in this regard, assuming that the first wireless communication apparatus 112a applies some other communication protocol/technique (such as BT BR/EDR or BLE), the second wireless communication apparatus 112b may be arranged to employ the WLAN technology referred to in the foregoing to establish the wireless link 102 with a wireless access point in its vicinity, which wireless link 102 enables the first monitoring device 110 to access the network 170 that further enables connection to the server device 150. As another example, the wireless communication apparatus 112b may be arranged to employ a cellular access technology known in the art to establish the wireless link 102 with a base station of a cellular network, which wireless link 102 enables the first monitoring device 110 to access the network 170 that further enables connection to the server device 150. Similar considerations are valid also for the second wireless communication apparatus 132b possibly included in the communication portion 132 of the second monitoring device 130 with respect to establishment of the wireless link 104.

Figure 4:
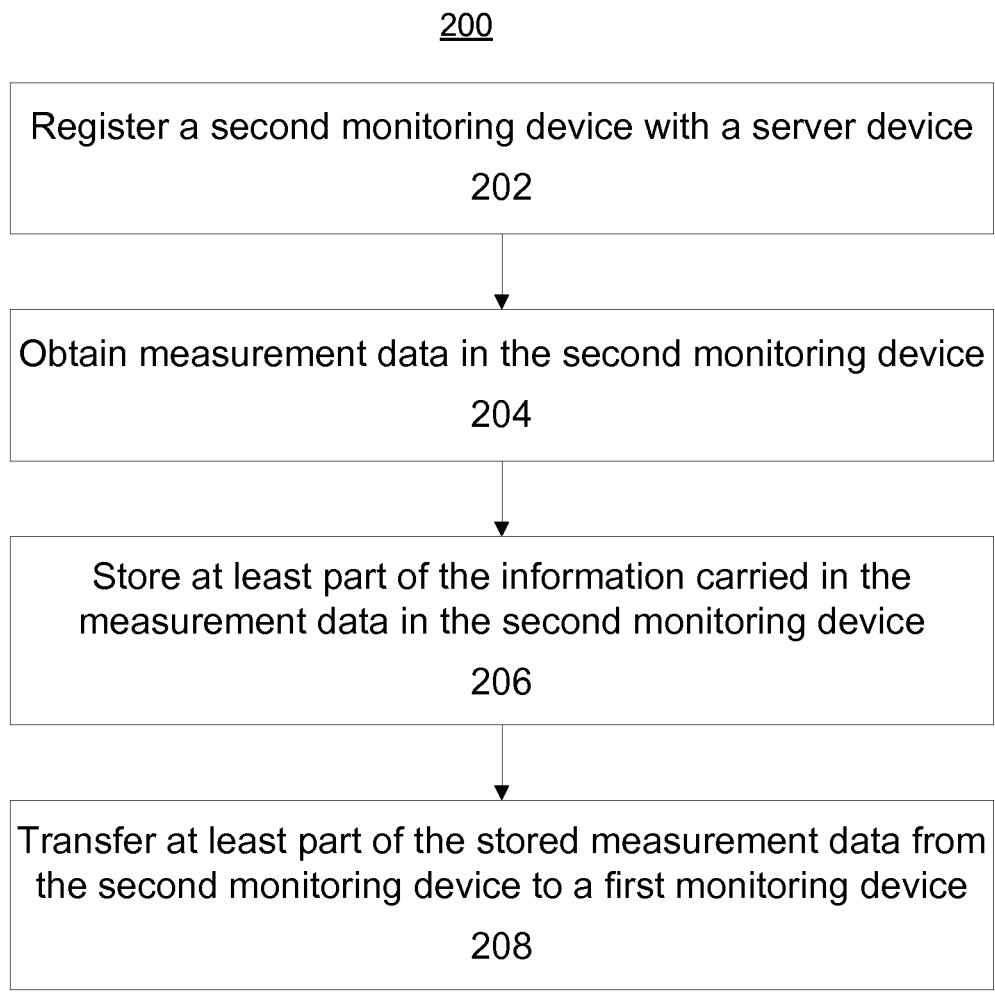
FIG. 4 illustrates a method according to an example embodiment.
Figure 5:
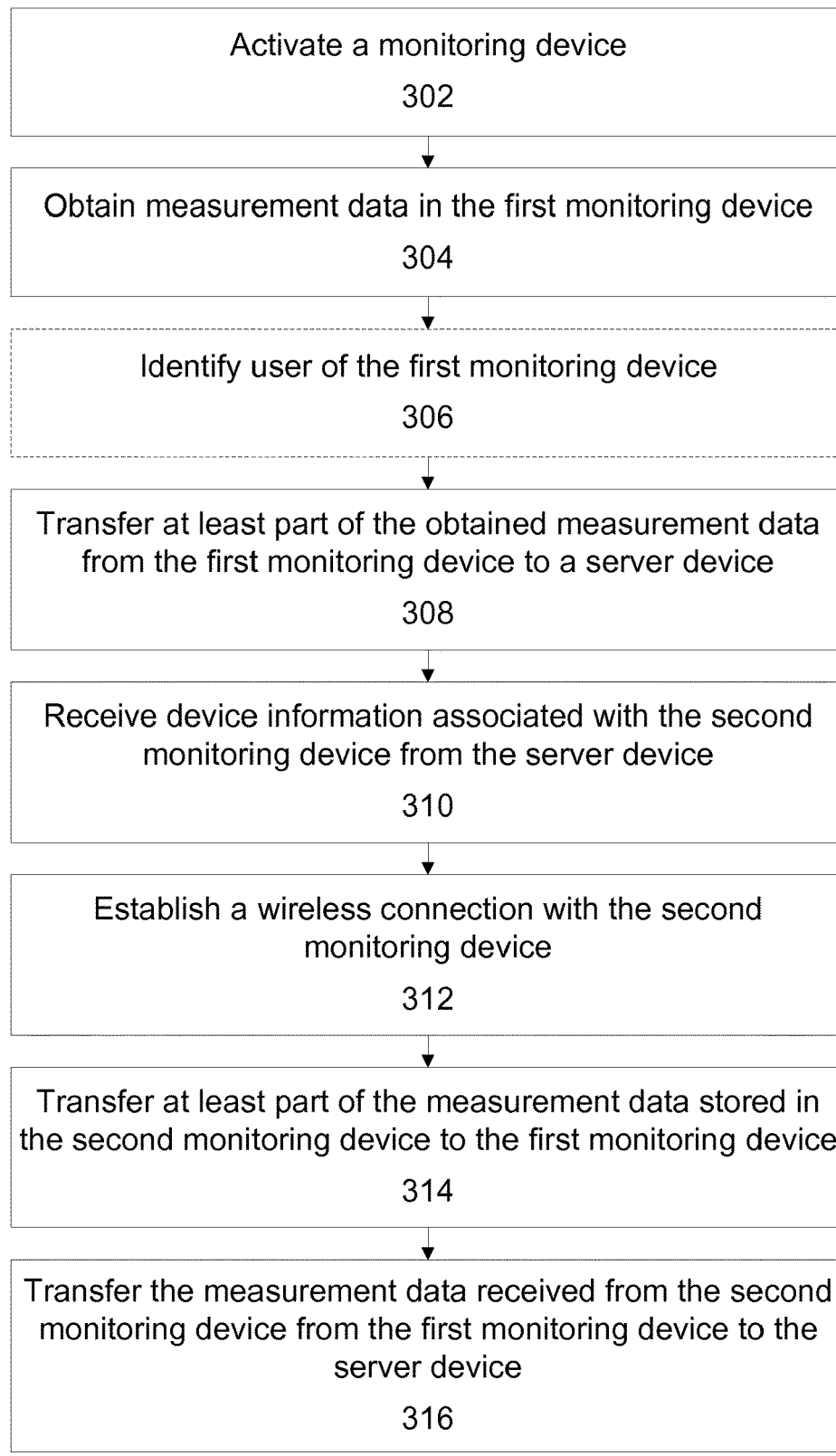
FIG. 5 illustrates a method according to an example embodiment.
Figure 6:
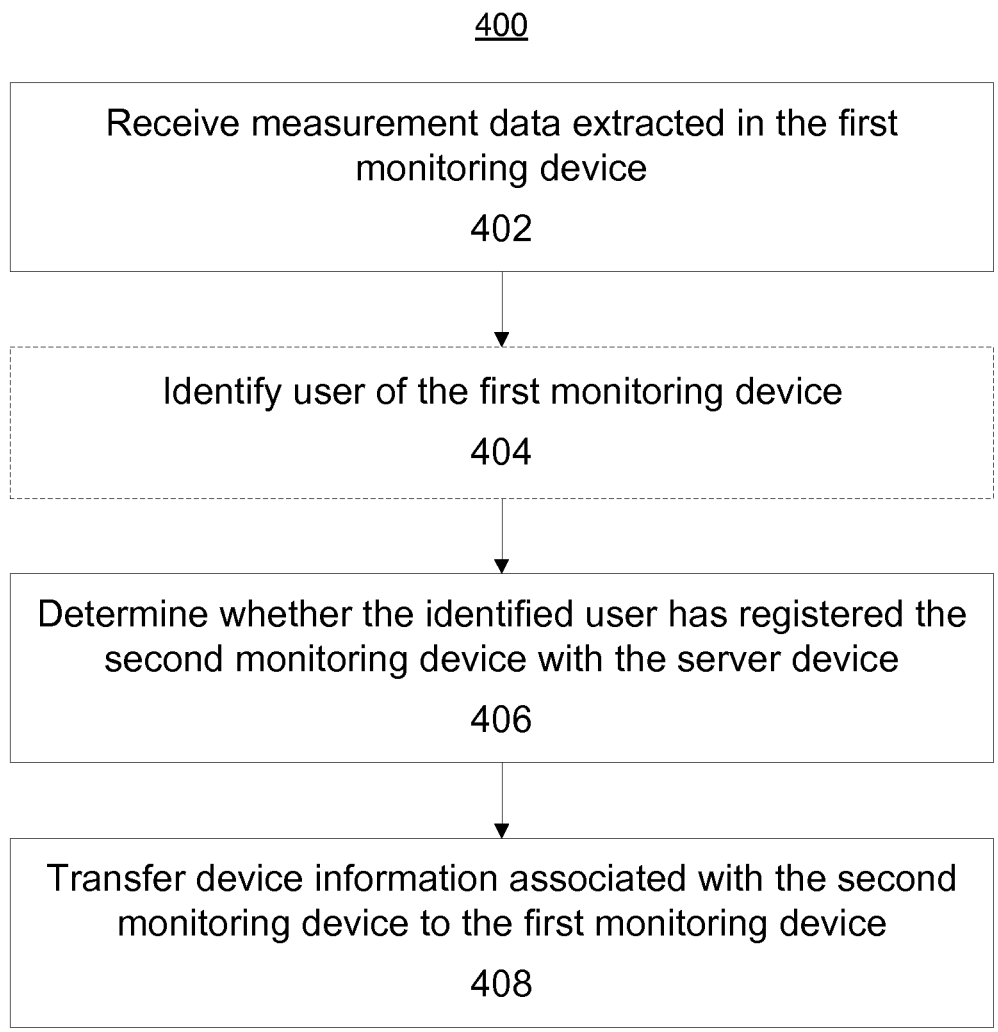
FIG. 6 illustrates a method according to an example embodiment.
Figure 7:
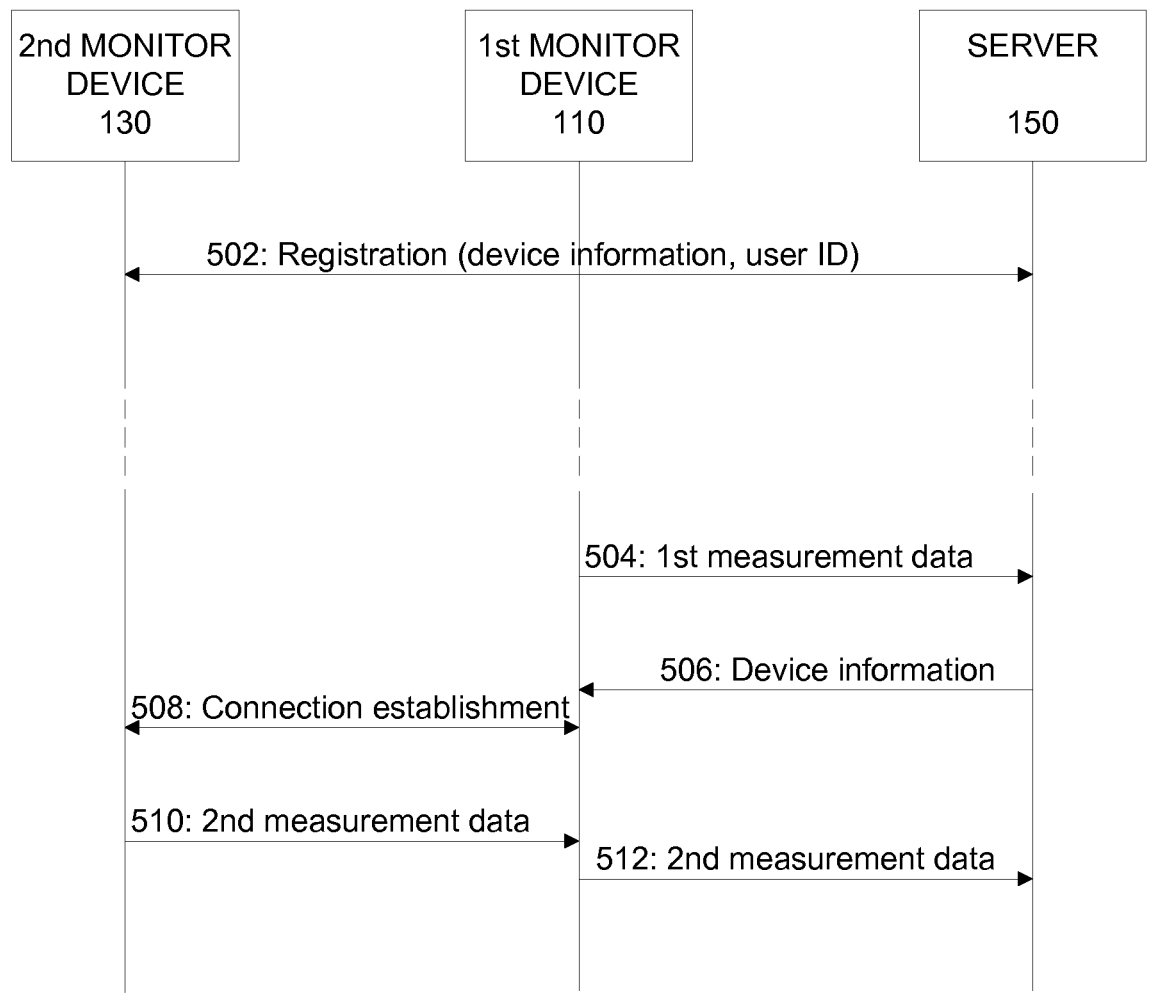
FIG. 7 depicts signaling between elements of the wireless communication arrangement according to an example embodiment.

FIG. 4 illustrates an exemplifying method 200 that may be carried out by the second monitoring device 130, FIG. 5 illustrates an exemplifying method 300 that may be carried out by the first monitoring device 110, and FIG. 6 illustrates an exemplifying method 400 that may be carried out by the server device 150, where each of the methods 200, 300 and 400 may be implemented, for example, within the framework of the wireless communication arrangement 100. Moreover, FIG. 7 depicts a signaling chart that serves to illustrate a non-limiting example of information exchange between the elements of the wireless communication arrangement 100 in context of methods 200, 300 and 400.

The method 200 commences by the second monitoring device 130 registering with the server device 150, as indicated in block 202. In an example, the registration may be carried out using a connection established via the wireless link 104. The registration procedure is represented in FIG. 7 by step 502 and the registration procedure may involve transferring one or more messages between the second monitoring device 130 and the server device 150. In another example, the registration is carried out by another device connected to the second monitoring device 130. In this regard, the second monitoring may employ the first communication apparatus 132a to establish a wireless link to a mobile device (such as a mobile phone, a smartphone, a tablet computer, a laptop computer, . . . ) that provides a connection to the server device 150 via the network 170. The mobile device further runs an application that enables controlling at least part of operation of the second monitoring device 130 and/or accessing the second measurement data stored in the second monitoring device 130. In such an arrangement the registration procedure may be carried out at least in part by the application running in the mobile device and using a connection between the mobile device and the second monitoring device 130 established via the wireless link.

The registration procedure results in storing, in a second user information database in the server device 150, at least a user identifier (user ID) assigned for the user of the second device 130 and device information associated with the second monitoring device 130. This device information may comprise a device identifier (device ID) assigned for the second device 130 and access information for establishing connection with the second monitoring device 130.

The user ID serves to uniquely identify the user at least in the framework of the wireless communication arrangement 100. In this regard, the user ID may be created or assigned as part of the registration procedure or the user ID may comprise (or be based on) in predefined user ID. The user ID may comprise, for example, the name of the user, a username assigned for the user, an email address of the user, a random or pseudo-random string of characters assigned to serve as identification of the user, etc. The device ID serves to uniquely identify the second monitoring device 130 at least in the framework of the wireless communication arrangement 100. The device ID may comprise, for example, a network address or a device address associated with the second monitoring device 130 or an identification of other type assigned to and/or selected by the second monitoring device 130. As an example, the device ID may comprise a MAC address assigned for the second communication apparatus 132b. The access information referred to above may comprise e.g. an authentication key and/or an encryption key that enable another device to establish a connection with the second monitoring device 130.

Although the second user information database is described herein as a single database, this is a non-limiting illustrative example chosen for editorial clarity and in general the second user information database may be provided as a combination of one or more databases and/or data storage structures of other types known in the art.

The registration (block 202) may by followed by the second monitoring device 130 obtaining the second measurement data, as indicated in block 204. In this regard, the control means in the second monitoring device 130 operates the sensor portion 139 to capture one or more second sensor signals and operates the analysis portion therein to process these captured second sensor signals into the one or more second measurement signals. As described in the foregoing, a second measurement signal may be indicative of an instantaneous value of the respective characteristic pertaining to the user or it may be indicative of the value of the respective characteristic as a function of time.

The second monitoring device 130 stores at least part of the information carried in the one or more second measurement signals in the memory 135 as the second measurement data for subsequent transfer to other devices, as indicated in block 206. In this regard, if considering a piece of the second measurement data extracted from a certain second measurement signal, the second measurement data may comprise, for example, a single value extracted from the certain second measurement signal, a time series or other subset of values extracted from the certain second measurement signal, or one or more values derived from a single value or from a time series or other subset of values extracted from the certain second measurement signal.

Referring to the example where the second monitoring device 130 is provided as the activity tracker, the second measurement data may include information that descriptive of distance traveled by the user, the number of steps taken by the user, the speed of movement of the user and/or heart rate of the user.

The method 200 continues with the second monitoring device 130 transferring the second measurement data to the first monitoring device 110, as indicate in block 208, for subsequent forwarding to the server device 150. The transfer of the second measurement data to the first monitoring device 110 is represented in FIG. 7 by step 510. The transfer may involve the second monitoring device 130 uploading the second measurement data to the first monitoring device 110 or the first monitoring device downloading the second measurement data from the second monitoring device 130. Before proceeding into description of examples concerning transfer of the second measurement data from the first monitoring device 110 onwards, some aspects of operation of the first monitoring device 110 in accordance with the method 300 are described first.

The method 300 commences by activating the first monitoring device 110, as indicated in block 302. The activation may involve the switching the first monitoring device 110 from off state to on state or from a sand-by state (or a power-saving state) to the on state. The activation may result from a user operating a switch (e.g. an on/off switch) of the UI of the first monitoring device 110 or from the user otherwise physically interacting with the first monitoring device 110 in a predefined manner.

Referring to the example where the first monitoring device 110 is provided as the digital weighing scale, the activation may comprise the first monitoring device 110 detecting the user stepping on the weighing scale.

The method 300 proceeds to obtaining the first measurement data, as indicated in block 304. In this regard, the control means in the first monitoring device 110 operates the sensor portion 119 to capture one or more first sensor signals and operates the analysis portion therein to process these captured first sensor signals into the one or more first measurement signals. As described in the foregoing, a first measurement signal may be indicative of an instantaneous value of the respective characteristic pertaining to the user or it may be indicative of the value of the respective characteristic as a function of time.

The first monitoring device 110 stores at least part of the information carried in the one or more first measurement signals in the memory 115 as the first measurement data for subsequent transfer to other devices. In this regard, if considering a piece of the first measurement data extracted from a certain first measurement signal, the first measurement data may comprise, for example, a single value extracted from the certain first measurement signal, a time series or other subset of values extracted from the certain first measurement signal, or one or more values derived from a single value or from a time series or other subset of values extracted from the certain first measurement signal.

Referring to the example where the first monitoring device 110 is provided as the digital weighing scale, the first measurement data may include indication of the weight of the user and the heart rate of the user.

In the course of the method 300, the first monitoring device 110 may identify the user, as indicated in block 306. As a result of user identification a user ID assigned for the identified user is stored at least temporarily in the memory 115. As described for the second device 130 in the foregoing, the user ID serves to uniquely identify the user at least in the framework of the wireless communication arrangement 100. In an example, the user identification is based on user input received via the UI of the first monitoring device 110. In this regard, the user input may directly indicate the user ID or the user ID may be derivable from the user input via mapping information available in the first monitoring device 110.

In another example, the user identification is automated and it is based at least in part on the first measurement data, on one or more of the first sensor signals and/or on one or more of the first measurement signals in comparison to corresponding data and/or signals obtained in the past. Such an automated method may involve verifying whether the first measurement data indicates for a certain characteristic a value that matches (e.g. is the same or close to) a predefined value associated with a certain user and considering the first measurement data to serve as identification of the certain user in case the verification is affirmative. In an example, such a predefined value may comprise a value obtained for the same characteristic in a recent past for the certain user. In a further example, the user identification is based on a combination of user input received via the UI of the first monitoring device 110 and the first measurement data, e.g. such that an automated method is applied first to find one or more potential users, respective identifications of the potential users are presented to the user via the UI and a user selection among the presented identifications is received via the UI and applied as identification of the user.

Referring to the example where the first monitoring device 110 is provided as the digital weighing scale, the user identification may be based on measured weight and/or heart rate of the user e.g. such that the measured weight and/or heart rate properties such as heart rate variability that are the same as or close to a weight and/or heart rate properties obtained for a certain user in the recent past results in identifying the measured weight and/or heart rate to pertain to the certain user.

Thereafter, the method 300 proceeds into transferring at least the first measurement data from the first monitoring device 110 to the server device 150 for storage therein, as indicated in block 308. This data transfer from the first monitoring device 110 to the server device 150 is represented in FIG. 7 by step 504. In an example, the user ID transferred from the first monitoring device 110 to the server device 150 together with the first monitoring data. The first measurement data and the user ID (if received) may be stored in a first user information database in the server device 150.

Although the first user information database is described herein as a single database, this is a non-limiting illustrative example chosen for editorial clarity and in general the first user information database may be provided as a combination of one or more databases and/or data storage structures of other types known in the art.

Referring now to the method 400, the server device 150 receives the first measurement data and the user ID from the first monitoring device, as indicated in block 402. Upon receiving these pieces of information the server device 150 stores them in the first user information database for subsequent analysis and/or provision for display to the user.

In alternative example, the user identification (block 306) in the first monitoring device 110 is omitted and only the first measurement data is transferred from the first monitoring device 110 to the server device 150. Consequently, the user identification to obtain the user ID may be carried out in the server device 150 instead, as indicated in block 404. In such an example, the user identification is provided as an automated procedure that is based on the first measurement data received from the first monitoring device 110. The user ID obtained via the automated procedure in the server device 110 is stored together with the first measurement data in the first user information database.

When in possession of the user ID, the server device 150 determines whether the same user has registered another device, e.g. the second monitoring device, as indicated in block 406. As an example in this regard, the server device 150 may search the second user information database in an attempt to identify a database entry that includes the user ID that matches the one received from the first monitoring device 110. If such a database entry is identified from the second user information database, the device information included in the identified database entry or parts thereof are extracted and transferred from the server device 150 to the first monitoring device 110, as indicated in block 408 and further represented in FIG. 7 by step 506. The device information transferred to the first monitoring device 110 includes the device ID and the access information for establishing connection with the second monitoring device 130, which in turn may include at least one of the authentication key and the encryption key assigned for the second monitoring device 130.

Referring to the example where the second monitoring device 130 is provided as the activity tracker, the search in the second user information database may result in extracting the device information associated with the activity tracker.

Referring back to the method 300, the first monitoring device 110 receives the device information from the server device 150, as indicated in block 310 (and represented in FIG. 7 by step 504). For the sake of an illustrative example, we may herein assume that the received device information serves to identify the second monitoring device 130. The first monitoring device 110 further makes use of the device information received from the server device 150 to establish the wireless link 106 and a connection between the first and second monitoring devices 110, 130 via the wireless link 106, as indicated in block 312 and represented in FIG. 7 by step 508.

Referring to the example where the first monitoring device 110 is provided as the digital weighing scale and the second monitoring device 130 is provided as the activity tracker, the operation(s) of the block 312 may involve the digital weighing scale establishing a wireless connection with the activity tracker.

The operations associated with the block 312 and/or step 508 may involve the first monitoring device 110 carrying out a device discovery procedure in order to detect presence of the second monitoring device 130. The device discovery may be based at least in part on the device information received from the server device 150 (e.g. the device ID) and it may be carried out using procedures known in the art. The device discovery procedure results in the first monitoring device 110 obtaining connection information that enables, together with the access information received from the server device, establishing the wireless link 106 to the second monitoring device 130. The connection information may be stored in the first monitoring device 110, e.g. in the memory 115, for subsequent connection attempts. If the first monitoring device 110 is already aware of the second monitoring device 130, the method 300 proceeds into reading the connection information from the memory 115. The first monitoring device applies the connection information together with the access information received from the server device 130 to establish the wireless link 106 and the connection between the first and second monitoring devices 110, 130 via the wireless link 106.

Once the connection between the first and second monitoring devices 110, 130 via the wireless link 106 has been established, the second measurement data stored in the second monitoring device 130 (e.g. in the memory 135 therein) is transferred to the first monitoring device 110, as indicated in block 314 and represented in FIG. 7 by step 510. In this regard, the first monitoring device 110 receives the second measurement data transmitted from the second monitoring device 130 in context of block 208 of the method 200. As described therein, the transfer of the second measurement data may involve the second monitoring device 130 uploading the second measurement data to the first monitoring device 110 or the first monitoring device downloading the second measurement data from the second monitoring device 130.

After reception of the second measurement data from the second monitoring device 130, the first monitoring device 110 transfers the second monitoring data to the server device 150 for storage and/or for presentation to the user therein, as indicated in block 316 and represented in FIG. 7 by step 512.

Referring to the example where the first monitoring device 110 is provided as the digital weighing scale and the second monitoring device 130 is provided as the activity tracker, the operation(s) of the blocks 314 and 316 may involve the digital weighing scale receiving one or more of information that descriptive of distance traveled by the user, the number of steps taken by the user, the speed of movement of the user and/or heart rate of the user from the activity tracker and forwarding this data to the server device 150.

Referring back to components of the first monitoring device 110 and the second monitoring device 130 depicted in FIGS. 2 and 3, respectively, the processor 116, 136 is configured to read from and write to the respective memory 115, 135. Although each of the processors 116, 136 is depicted as a respective single component, any of the processors 116, 136 may be implemented as respective one or more separate processing components. Similarly, although each of the memories 115, 135 is depicted as a respective single component, any of the memories 115, 135 may be implemented as respective one or more separate components, some or all of which may be integrated/removable and/or may provide permanent/semi-permanent/dynamic/cached storage.

The memory 115, 135, may store the respective computer program 117, 137 comprising computer-executable instructions that control the operation of the respective monitoring device 110, 130 when loaded into the respective processor 116, 136. As an example, the computer program 117 may include one or more sequences of one or more instructions. The computer program 117 may be provided as a computer program code. The processor 116 is able to load and execute the computer program 117 by reading the one or more sequences of one or more instructions included therein from the memory 115. The one or more sequences of one or more instructions may be configured to, when executed by the processor 116, cause the first monitoring device 110 to carry out operations, procedures and/or functions described in the foregoing. Hence, the first monitoring device 110 may comprise at least one processor 116 and at least one memory 115 including computer program code for one or more programs, the at least one memory 115 and the computer program code configured to, with the at least one processor 116, cause the first monitoring device 110 to perform operations, procedures and/or functions described in the foregoing. Similar considerations are equally valid for corresponding components 13x of the second monitoring device 130.

Each of the computer programs 117, 137 may be provided e.g. as a respective computer program product comprising at least one computer-readable non-transitory medium having program code stored thereon, the program code, when executed by the respective monitoring device 110, 130, causes the monitoring device 110, 130 at least to perform operations, procedures and/or functions described in the foregoing in context of the respective monitoring device 110, 130. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described.

Although functions have been described with reference to certain features, those functions may be performable by other features whether described or not. Although features have been described with reference to certain embodiments, those features may also be present in other embodiments whether described or not.

The invention claimed is:

1. A method, in a device comprising a sensor portion for deriving, on basis of one or more sensor signals that are descriptive of respective physical characteristic pertaining to a user, at least one measurement signal that is descriptive of a characteristic pertaining to the user, the method comprising:
   obtaining first measurement data that comprises one or more values indicated by the at least one measurement signal and transferring the first measurement data to a server device over a first wireless link;
   receiving, from the server device, device information that comprises at least a device identifier and access information for another device that is capable of providing second measurement data that is descriptive of one or more characteristics pertaining to the same user;
   in response to receiving said device information, detecting presence of said another device and establishing a second wireless link with said another device using said device information; and
   receiving the second measurement data from said another device via the second wireless link and transferring the second measurement data to the server device via the first wireless link.

2. The method of claim 1, further comprising identifying the user at least in part on basis of the at least one measurement signal and transferring an identification of the user to the server device together with the first measurement data.

3. The method of claim 2, further comprising identifying the user at least in part on basis of past values obtained for the at least one measurement signal.

4. The method of claim 1, further comprising identifying the user at least in part on basis of user input received via a user interface of the device.

5. The method of claim 1, wherein detecting presence of said another device comprises carrying out a device discovery procedure to detect presence of a device having said device identifier assigned thereto.

6. The method of claim 1, wherein said access information comprises at least one of an authentication key or an encryption key and wherein establishing the second wireless link comprises establishing the second wireless link using at least one of said authentication key or said encryption key.

7. The method of claim 1, further comprising activating the device; and
   obtaining the first measurement data and transferring the first measurement data to
   the server device in response to activating the device.

8. A non-transitory computer readable medium comprising program instructions for causing a device to perform at least the following:
   obtaining first measurement data that comprises one or more values indicated by at least one measurement signal descriptive of respective physical characteristic pertaining to a user;
   transferring the first measurement data to a server device over a first wireless link;
   receiving, from the server device, device information that comprises at least a device identifier and access information for another device that is capable of providing second measurement data that is descriptive of one or more characteristics pertaining to the same user;
   in response to receiving said device information, detecting presence of said another device and establishing a second wireless link with said another device using said device information; and
   receiving the second measurement data from said another device via the second wireless link and transferring the second measurement data to the server device via the first wireless link.

9. A device comprising:
   a sensor portion for deriving, on basis of one or more sensor signals that are descriptive of respective physical characteristic pertaining to a user, at least one measurement signal that is descriptive of a characteristic pertaining to the user;
   a communication apparatus for wireless communication over a wireless link; and a control portion configured to cause the device to perform at least the following:

obtain first measurement data that comprises one or more values indicated by the at least one measurement signal and transfer the first measurement data to a server device over a first wireless link;

receive, from the server device, device information that comprises at least a device identifier and access information for another device that is capable of providing second measurement data that is descriptive of one or more characteristics pertaining to the same user;

in response to receiving said device information, detect presence of said another device and establish a second wireless link with said another device using said device information, and receive the second measurement data from said another device via the second wireless link and transfer the second measurement data to the server device via the first wireless link.

10. The device of claim 9, wherein the control portion is further configured to identify the user at least in part on basis of the at least one measurement signal, and transfer an identification of the user to the server device together with the first measurement data.

11. The device of claim 10, wherein identifying the user at least in part on basis of past values obtained for the at least one measurement signal.

12. The device of claim 9, wherein the control portion is further configured to identify the user at least in part on basis of user input received via a user interface of the device.

13. The device of claim 9, wherein detecting presence of said another device comprises carrying out a device discovery procedure to detect presence of a device having said device identifier assigned thereto.

14. The device of claim 9, wherein said access information comprises at least one of an authentication key or an encryption key, and wherein establishing the second wireless link comprises establishing the second wireless link using at least one of said authentication key or said encryption key.

15. The device of claim 9, wherein the control portion is further configured to activate the device; and obtain the first measurement data and transfer the first measurement data to the server device in response to activating the device.

16. The device of claim 15, wherein activating the device comprises activating the device in response to a user physically interacting with the device in a predefined manner.

17. The device of claim 9, wherein said first measurement data is indicative of one or more of a biometric characteristic of the user and a physical state of the user.

18. The device of claim 9, wherein said first measurement data is indicative one or more of a weight of the user, and a heart rate of the user.

19. The device of claim 9, wherein said second measurement data is indicative of one or more of a biometric characteristic of the user, and a physical state of the user.

20. The device of claim 9, wherein said second measurement data is indicative one or more of a distance travelled by the user, the number of steps taken by the user, a speed of movement of the user, and a heart rate of the user.

* * * * *